United States Patent
Ye et al.

(10) Patent No.: US 9,892,527 B2
(45) Date of Patent: Feb. 13, 2018

(54) DEVELOPMENT OF ITERATIVE RECONSTRUCTION FRAMEWORK USING ANALYTIC PRINCIPLE FOR LOW DOSE X-RAY CT

(71) Applicant: Korea Advanced Institute of Science and Technology, Yuseong-gu, Daejeon (KR)

(72) Inventors: Jong Chul Ye, Daejeon (KR); Eun Hee Kang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 15 days.

(21) Appl. No.: 14/886,745

(22) Filed: Oct. 19, 2015

(65) Prior Publication Data
US 2016/0328842 A1  Nov. 10, 2016

(30) Foreign Application Priority Data
May 7, 2015  (KR) .................. 10-2015-0064033

(51) Int. Cl.
*G06K 9/00* (2006.01)
*G06T 11/00* (2006.01)
*A61B 6/03* (2006.01)
*A61B 6/00* (2006.01)

(52) U.S. Cl.
CPC .......... *G06T 11/005* (2013.01); *G06T 11/006* (2013.01); *A61B 6/032* (2013.01); *A61B 6/5205* (2013.01); *A61B 6/542* (2013.01); *G06T 2211/424* (2013.01)

(58) Field of Classification Search
None
See application file for complete search history.

(56) References Cited

U.S. PATENT DOCUMENTS

| | | | | |
|---|---|---|---|---|
| 2007/0297661 A1* | 12/2007 | Zhu | ........................ | G06T 11/006 382/131 |
| 2009/0010518 A1* | 1/2009 | Schoendube | ......... | G06T 11/006 382/131 |
| 2009/0196393 A1* | 8/2009 | Wang | .................... | G06T 11/006 378/4 |
| 2010/0121183 A1* | 5/2010 | Taguchi | ............... | A61B 6/5264 600/427 |
| 2011/0052021 A1* | 3/2011 | Noo | ........................ | A61B 6/032 382/131 |

(Continued)

OTHER PUBLICATIONS

Tang, S., Yang, Y., & Tang, X. (Feb. 2012). Interior tomography with radial Hilbert filtering and a priori information in a small circular area. In Proc. of SPIE Vol (vol. 8313, pp. 831335-1).*

(Continued)

*Primary Examiner* — Vu Le
*Assistant Examiner* — Samah Beg
(74) *Attorney, Agent, or Firm* — Fenwick & West LLP

(57) ABSTRACT

Disclosed is a method of reconstructing an image. The method of reconstructing an image includes receiving low dose X-ray computed tomography (CT) data, applying an analytic principle to an optimization approach for low dose imaging to transform the low dose X-ray CT data, and removing a noise included in the low dose X-ray CT data to reconstruct a high-quality image.

13 Claims, 5 Drawing Sheets

(56) References Cited

U.S. PATENT DOCUMENTS

| | | | | |
|---|---|---|---|---|
| 2011/0142311 | A1* | 6/2011 | Felsberg | G06T 11/006 382/131 |
| 2012/0039434 | A1* | 2/2012 | Wang | A61B 6/027 378/11 |
| 2012/0063659 | A1* | 3/2012 | Wang | G06T 11/006 382/131 |
| 2012/0301008 | A1* | 11/2012 | Dennerlein | G06T 11/006 382/132 |
| 2013/0251224 | A1* | 9/2013 | Zou | G06T 11/006 382/131 |
| 2014/0226783 | A1* | 8/2014 | Ning | A61B 6/032 378/5 |
| 2014/0334701 | A1* | 11/2014 | Ye | G06T 11/006 382/131 |
| 2015/0030227 | A1* | 1/2015 | Liang | G06T 11/006 382/131 |
| 2015/0139526 | A1* | 5/2015 | Jeong | A61B 6/032 382/132 |
| 2015/0193927 | A1* | 7/2015 | Wang | G01T 1/1647 382/131 |
| 2015/0287223 | A1* | 10/2015 | Bresler | G06T 11/006 382/131 |
| 2016/0223475 | A1* | 8/2016 | Palamodov | G06T 11/006 |
| 2016/0350944 | A1* | 12/2016 | Pal | G06T 11/005 |

OTHER PUBLICATIONS

Lü, D. H., & Shi, A. S. (2010). Reconstruction method of differentiated backprojection-projection onto convex sets in the interior problem and design of bone-nail model. Journal of Shanghai University (English Edition), 14, 131-136.*

Zou, Y., & Pan, X. (2004). Exact image reconstruction on PI-lines from minimum data in helical cone-beam CT. Physics in Medicine and Biology, 49(6), 941.*

Sidky, E. Y., & Pan, X. (2008). Image reconstruction in circular cone-beam computed tomography by constrained, total-variation minimization. Physics in medicine and biology, 53(17), 4777.*

Noo, F., Clackdoyle, R., & Pack, J. D. (2004). A two-step Hilbert transform method for 2D image reconstruction. Physics in Medicine and Biology, 49(17), 3903-3923.*

Bin, Y., Lin, D., Yu, H., Feng, Z., Xian-Chao, W., & Lei, L. (2014). Fast local reconstruction by selective backprojection for low dose in dental computed tomography. Chinese physics C, 38(10), 108201.*

Ye, Y., Yu, H., Wei, Y., & Wang, G. (2007). A general local reconstruction approach based on a truncated Hilbert transform. Journal of Biomedical Imaging, 2007(1), 2-2.*

Zeng, G. L. (2007). Image reconstruction via the finite Hilbert transform of the derivative of the backprojection. Medical physics, 34(7), 2837-2843.*

* cited by examiner

PI-line

Cartesian coordinate

DEVELOPMENT OF ITERATIVE RECONSTRUCTION FRAMEWORK USING ANALYTIC PRINCIPLE FOR LOW DOSE X-RAY CT

CROSS-REFERENCE TO RELATED APPLICATIONS

A claim for priority under 35 U.S.C. §119 is made to Korean Patent Application No. 10-2015-0064033 filed May 7, 2015, in the Korean Intellectual Property Office, the entire contents of which are hereby incorporated by reference.

BACKGROUND

The inventive concepts described herein relate to a technology for reconstructing an image, and more particularly, relate to a method that reconstructs a high quality image by removing a noise in the image.

X-ray computed tomography (CT) refers to a technique for obtaining a high-quality image about the inner part of a human body by outputting a X-ray to the human body and detecting the X-ray passing through the human body. The X-ray CT is classified into a method of obtaining a 2-dimensional reconstruction image through a photography system including a radiation emission unit and a 1-dimensional detection unit and a method of obtaining a 3-dimensional reconstruction image through a photography system including a radiation emission unit and a 2-dimensional detection unit. Both of the two methods are used according to purposes and situations of a medical examination. Also, a method in which a trajectory of a radiation emission unit is helical has been developed to diagnose the whole human body.

However, the probability that a human body is exposed to a X-ray increases when X-ray is used, thereby causing cancers. Accordingly, low dose CT for reducing radiation dose in CT and minimizing exposed dose has been developed. An image signal obtained by the low dose CT includes a noise based on Poisson distribution. Because an image reconstructed in a conventional reconstruction method includes a noise, it is difficult to examine an internal state of a human body. An iterative reconstruction method is used to obtain a high-quality reconstruction image in which a noise is removed. A model based iterative reconstruction (MBIR) method is a representative iterative reconstruction method. The MBIR method iteratively reconstructs the high-quality reconstruction image by modeling the CT system.

The low dose X-ray CT may be modeled according to Equation 1.

$$y = A\mu + \omega. \quad \text{[Equation 1]}$$

In the equation 1, "y" means projection data measured from a detection unit. "A" means a projector generating projection data. "$\mu$" is an image to be reconstructed. "$\omega$" means a noise based on Poisson distribution. The following optimization problem may be solved to obtain a reconstruction image "$\mu$" in which a noise is removed.

$$\min_{\mu} \|y - A\mu\|^2 + \lambda R(\mu) \quad \text{[Equation 2]}$$

"$\lambda$" means an adjustment parameter, and "$R(\mu)$" means a regularization term. To solve the optimization problem, a projector A and a backprojector $A^T$ that performs a backprojection process with respect to projection data are repeated in order. The conventional iterative reconstruction method will be described with reference to FIG. 3. However, the above-described manner causes an increase in computation, and thus, it takes a long time to reconstruct an image.

SUMMARY

One aspect of embodiments of the inventive concept is directed to provide a method of reconstructing a high quality image, in which noise is removed, through low dose CT, thereby making it possible to obtain a reconstruction time practically usable.

Another aspect of embodiments of the inventive concept is directed to provide a method of reconstructing an image includes receiving low dose X-ray computed tomography (CT) data, applying an analytic principle to an optimization approach to transform the low dose X-ray CT data, and removing a noise included in the low dose X-ray CT data to reconstruct a high-quality image.

The application of the analytic principle may include transforming the low dose X-ray CT data in the form for iteratively solving an optimization problem included in the optimization approach using a preconditioner.

The application of the analytic principle may include increasing a reconstruction speed by applying a differentiated backprojector as a preconditioner in the method in which an image is reconstructed using the analytic principle.

Differentiated backprojection (DBP) data may be generated by performing the differentiated backprojector for performing differentiation with respect to projection data and for performing a backprojection process with respect to the differentiated projection data based on a PI-line. The DBP data on the PI-line may have a Hilbert transform relation with a reconstruction image on the PI-line.

The application of the analytic principle may include defining an operator T as a transform operator for transforming an updated image on Cartesian coordinate into an image on the PI-line in the method using the analytic principle.

The application of the analytic principle may include redefining an optimization problem using a projector and a backprojector as an optimization problem using a Hilbert transform operator and a transform operator for transforming an updated image on Cartesian coordinate into an image on the PI-line by applying a differentiated backprojector as a preconditioner to the optimization problem using the projector and the backprojector.

The application of the analytic principle may include applying a regularization term and redefining an optimization problem to remove a noise.

The application of the analytic principle may include applying the method to the low dose X-ray CT data after applying a Hilbert transform to DBP data to transform the DBP data, to which the Hilbert transform is applied, into a reconstruction image on a PI-line or after performing an initial reconstruction using an analytic reconstruction algorithm, for a convergence speed that is equal to or greater than a predetermined reference speed.

Still another aspect of embodiments of the inventive concept is directed to provide a CT system for reconstructing an image includes a reception unit for receiving low dose X-ray CT data, a transform unit for applying an analytic principle to an optimization approach to transform the low dose X-ray CT data, and a reconstruction unit for removing a noise included in the low dose X-ray CT data and reconstruct a high-quality image.

The transform unit may transform the low dose X-ray CT data into a form for iteratively solving an optimization problem included in the optimization approach using a preconditioner.

The transform unit may increase a reconstruction speed by applying a differentiated backprojector as a preconditioner in an image reconstruction method using the analytic principle.

DBP data may be generated by performing the differentiated backprojector for performing differentiation with respect to projection data and for performing a backprojection process with respect to the differentiated projection data based on a PI-line. The DBP data on the PI-line may have a Hilbert transform relation with a reconstruction image on the PI-line.

The transform unit may define an operator T as a transform operator for transforming an updated image on Cartesian coordinate into an image on the PI-line in an iterative reconstruction using the analytic principle.

The transform unit may redefine an optimization problem using a projector and a backprojector as an optimization problem using a Hilbert transform operator and a transform operator for transforming an updated image on Cartesian coordinate into an image on the PI-line by applying a differentiated backprojector as a preconditioner to the optimization problem using the projector and the backprojector.

The transform unit may apply a regularization term and redefines an optimization problem to remove a noise.

The transform unit may apply the image reconstruction method to the low dose X-ray CT data after applying a Hilbert transform to DBP data to transform the DBP data, to which the Hilbert transform is applied, into a reconstruction image on PI-line or after performing an initial reconstruction using an analytic reconstruction algorithm, for a convergence speed that is equal to or greater than a predetermined reference speed.

Yet another aspect of embodiments of the inventive concept is directed to provide a computer-readable recording medium recorded with an instruction for reconstructing an image by a computer system. The instruction, when executed by the computer system, causing the computer system to perform a method. The method includes receiving low dose X-ray CT data, applying an analytic principle to an optimization approach to transform the low dose X-ray CT data, and removing a noise included in the low dose X-ray CT data to reconstruct a high-quality image.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
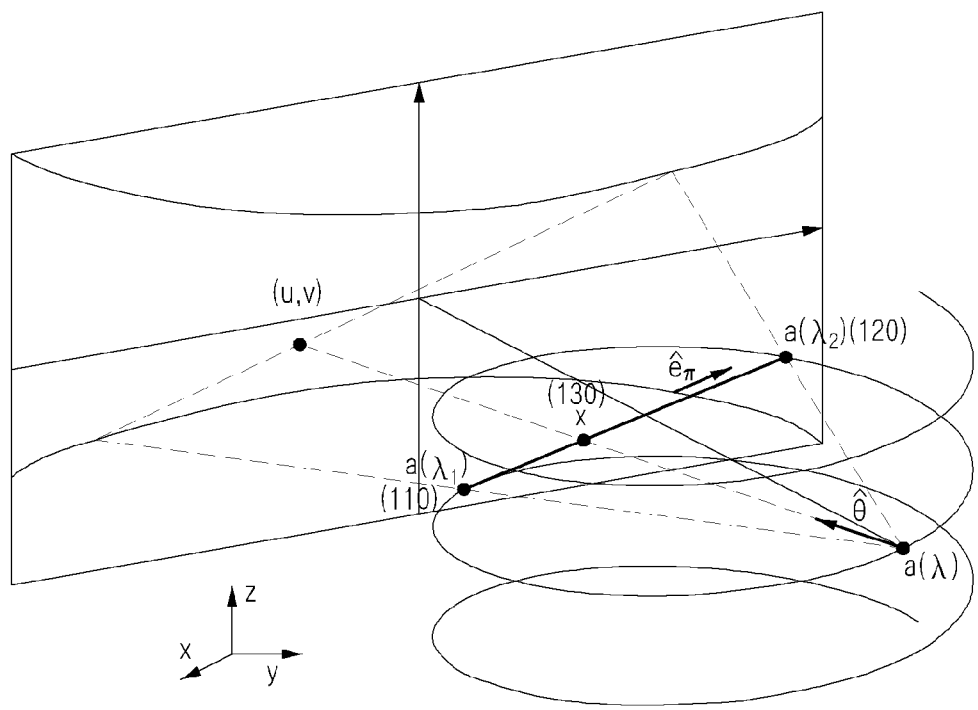
FIG. 1 is a diagram illustrating a trajectory of a radiation emission unit of a helical CT system and a PI-line, according to an embodiment of the inventive concept.

Embodiments will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the concept of the inventive concept to those skilled in the art. Accordingly, known processes, elements, and techniques are not described with respect to some of the embodiments of the inventive concept. Unless otherwise noted, like reference numerals denote like elements throughout the attached drawings and written description, and thus descriptions will not be repeated. In the drawings, the sizes and relative sizes of layers and regions may be exaggerated for clarity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Also, the term "exemplary" is intended to refer to an example or illustration.

It will be understood that when an element or layer is referred to as being "on", "connected to", "coupled to", or "adjacent to" another element or layer, it can be directly on, connected, coupled, or adjacent to the other element or layer, or intervening elements or layers may be present. In contrast, when an element is referred to as being "directly on," "directly connected to," "directly coupled to," or "immediately adjacent to" another element or layer, there are no intervening elements or layers present.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

For helical computed tomography (CT), a trajectory vector a of a radiation emission unit may be expressed according to Equation 3.

$$a(\lambda) = \left(R\cos\lambda, R\sin\lambda, \frac{h}{2\pi}\lambda\right)\qquad\text{[Equation 3]}$$

"λ" may mean a rotation angle of the radiation emission unit. "R" may mean a helical radius. "h" may mean a helical pitch.

Figure 2:
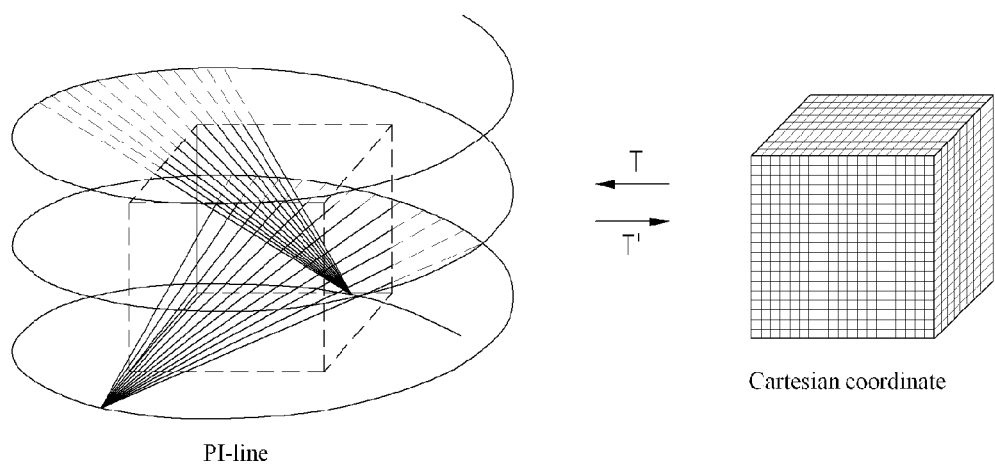
FIG. 2 is a diagram for describing a transform relation between a Cartesian coordinate system and a PI-line.

FIG. 1 is a diagram illustrating a trajectory of a radiation emission unit of a helical CT system and a PI-line, according to an embodiment of the inventive concept, and FIG. 2 is a diagram for describing a transform relation between a Cartesian coordinate system and a PI-line.

A PI-line illustrated in FIG. 1 may be a straight line connecting the two points $a(\lambda_1)$ 110 and $a(\lambda_2)$ 120 which satisfy $0<\lambda_2-\lambda_1<2\pi$ on a helical trajectory vector a, and the PI-line may uniquely exist with respect to a helical internal point x 130.

A helical cone-beam projection image may be described according to Equation 4.

$$D_\mu(a,\theta)=\int_0^\infty dt\mu(a+t\theta).\qquad\text{[Equation 4]}$$

θ may mean a direction vector of X-ray emitted from the radiation emission unit.

First, a differentiated backprojection (DBP) signal may be calculated according to Equation 5 to reconstruct an attenuation coefficient μ from a projection image $D_\mu(a, \theta)$.

$$g(x) = -\frac{1}{2\pi}\int_{\lambda_1}^{\lambda_2}\frac{d\lambda}{|x-a(\lambda)|}\frac{\partial}{\partial q}D_\mu(a(q),\theta)\bigg|_{q=\lambda}\qquad\text{[Equation 5]}$$

g(x) and μ(x) may have a Hilbert transform relation with each other as expressed by Equation 6.

$$g(x) = \frac{1}{\pi}P.V.\int_{-\infty}^{\infty}\frac{dx'}{x-x'}\mu(x') = \mathcal{H}\mu(x)\qquad\text{[Equation 6]}$$

P.V. may mean a Cauchy principal value, and operator $\mathcal{H}$ may mean a Hilbert transform.

A preconditioner may be used to accelerate a convergence speed in a conventional iterative method and should not amplify a noise. A differentiated backprojector may be provided as a preconditioner. The differentiated backprojector may be defined according to Equation 7.

$$DBP\{\cdot\} = \int_{\lambda_1}^{\lambda_2}\frac{1}{\|x'-a(\lambda)\|}\frac{\partial\{\cdot\}}{\partial q}\bigg|_{q=\lambda}\qquad\text{[Equation 7]}$$

λ may mean an angle by which the radiation emission unit is rotated. a(λ) may mean a point on a trajectory of the radiation emission unit. x' may mean a point on the PI-line connecting $a(\lambda_1)$ and $a(\lambda_2)$. $\lambda_1$ and $\lambda_2$ may satisfy a condition $0<\lambda_2-\lambda_1<2\pi$. Here, the differentiated backprojector may include a differential operation and a backprojection operation for performing a backprojection process with respect to a differentiated projection data based on a PI-line, and should not amplify a noise.

The optimization problem for obtaining an image in which a noise is removed using the differentiated backprojector may be newly redefined.

$$\min_x\|g - \mathcal{H}Tx\|^2 + \lambda R(x)\qquad\text{[Equation 8]}$$

g may mean data obtained by performing the differentiated backprojection process with respect to projection data. Operator $\mathcal{H}$ may be for a Hilbert transform. Operator T may mean an operator that transforms Cartesian coordinate into the PI-line. A new iterative reconstruction method will be described with reference to FIG. 4. Because operators $\mathcal{H}$ and T have lower computational complexities than the projector A and the backprojector $A^T$, reconstruction time may be reduced.

Figure 3:
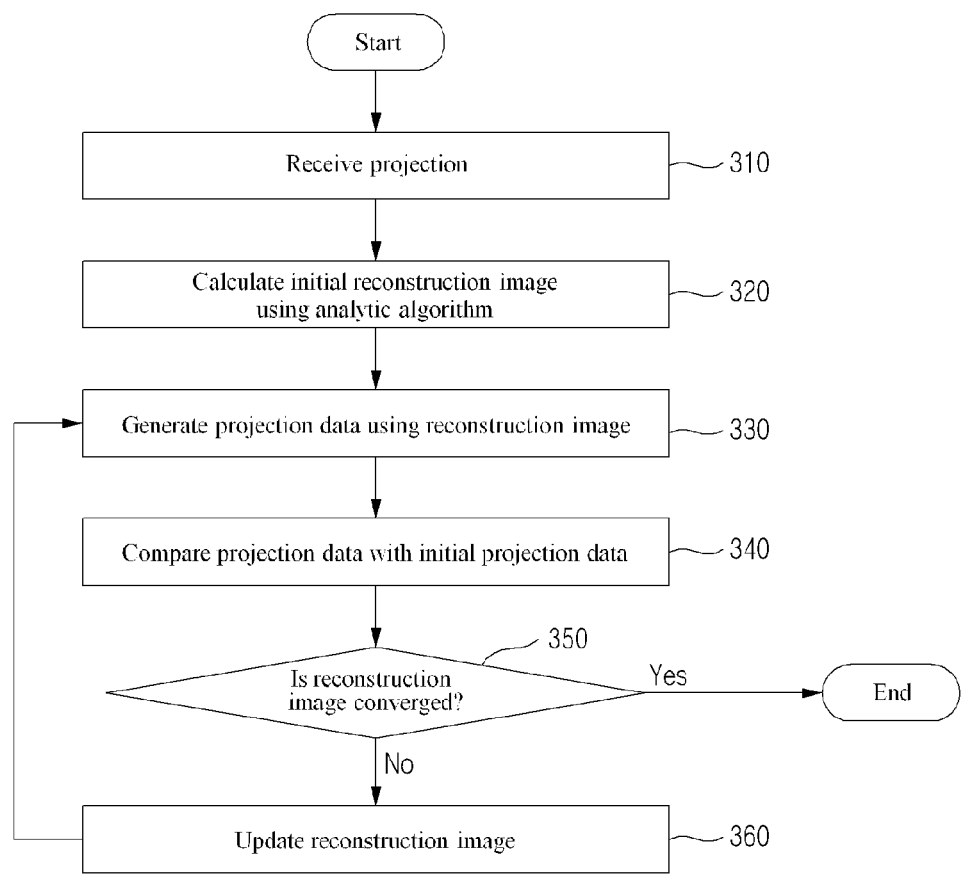
FIG. 3 is a flow chart for schematically describing an iterative reconstruction method according to a related art.

FIG. 3 is a flow chart for schematically describing an iterative reconstruction method according to a related art.

In a conventional iterative reconstruction method, a projection may be received (310). An initial reconstruction image may be calculated using an analytic algorithm in response to receiving the projection (320). Projection data may be generated using a reconstruction image (330). Initial projection data may be compared with the generated projection data (340). Whether the reconstruction image is converged may be determined according to comparing the initial projection data with the projection data (350). If the reconstruction image is converged, the conventional iterative reconstruction method may be ended. If the reconstruction image is not converged, the reconstruction image may be updated (360).

Figure 4:
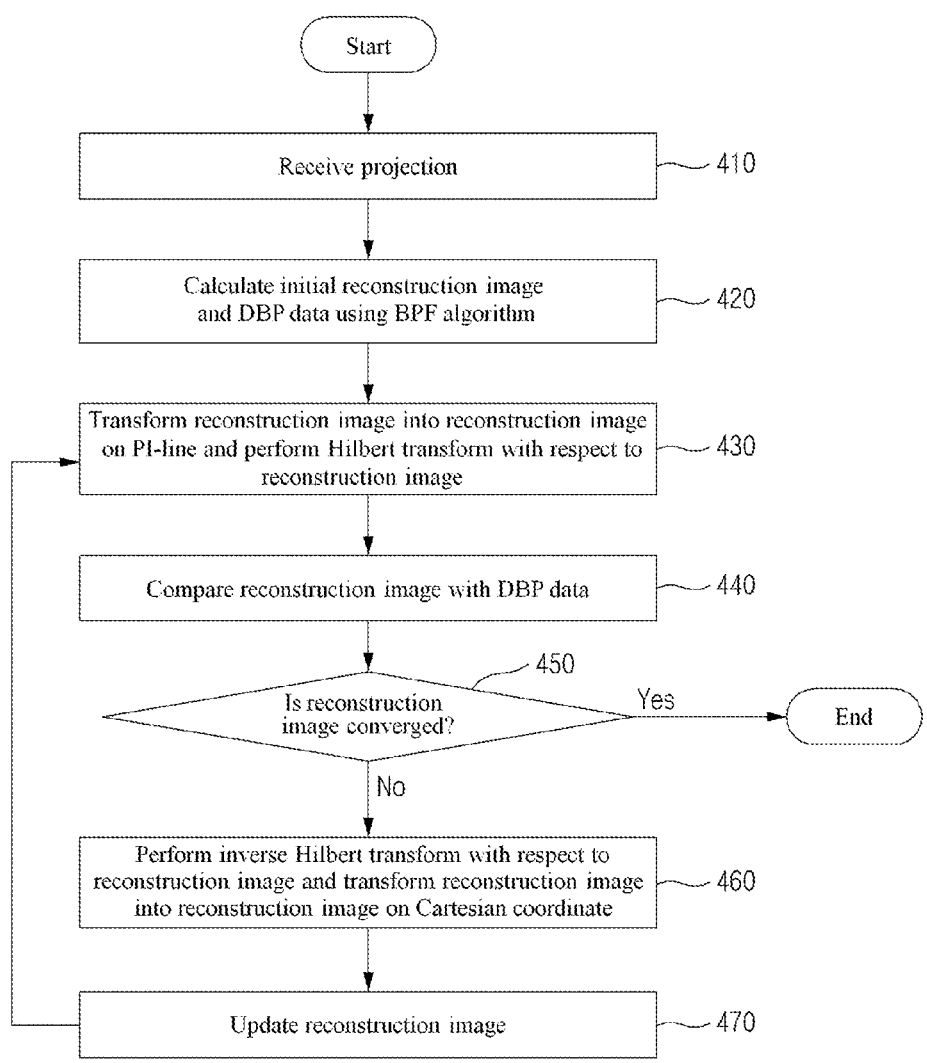
FIG. 4 is a flow chart for describing a method of iteratively reconstructing an image, according to an embodiment of the inventive concept.

FIG. 4 is a flow chart for describing a method for iteratively reconstructing an image, according to an embodiment of the inventive concept.

A CT system may receive a projection (410). The CT system may calculate an initial reconstruction image and DBP data using a back projection filtration (BPF) algorithm, upon receiving the projection (420). The CT system may transform a reconstruction image into a reconstruction image on a PI-line, and may perform a Hilbert transform with respect to the reconstruction image (430). The CT system may compare the DBP data with the reconstruction image, in which the Hilbert transform is performed (440). The CT system may determine whether the reconstruction image is converged (450). If the reconstruction image is converged, the CT system may end the process. Moreover, if the reconstruction image is not converged, the CT system may perform an inverse Hilbert transform with respect to the reconstruction image and may transform the reconstruction image into a reconstruction image on Cartesian coordinate (460). After performing an inverse Hilbert transform, the CT system may update the reconstruction image which is transformed into a reconstruction image on Cartesian coordinate (470). Here, the CT system may repeat the operations 430 to 470 when the reconstruction image is updated.

Figure 5:
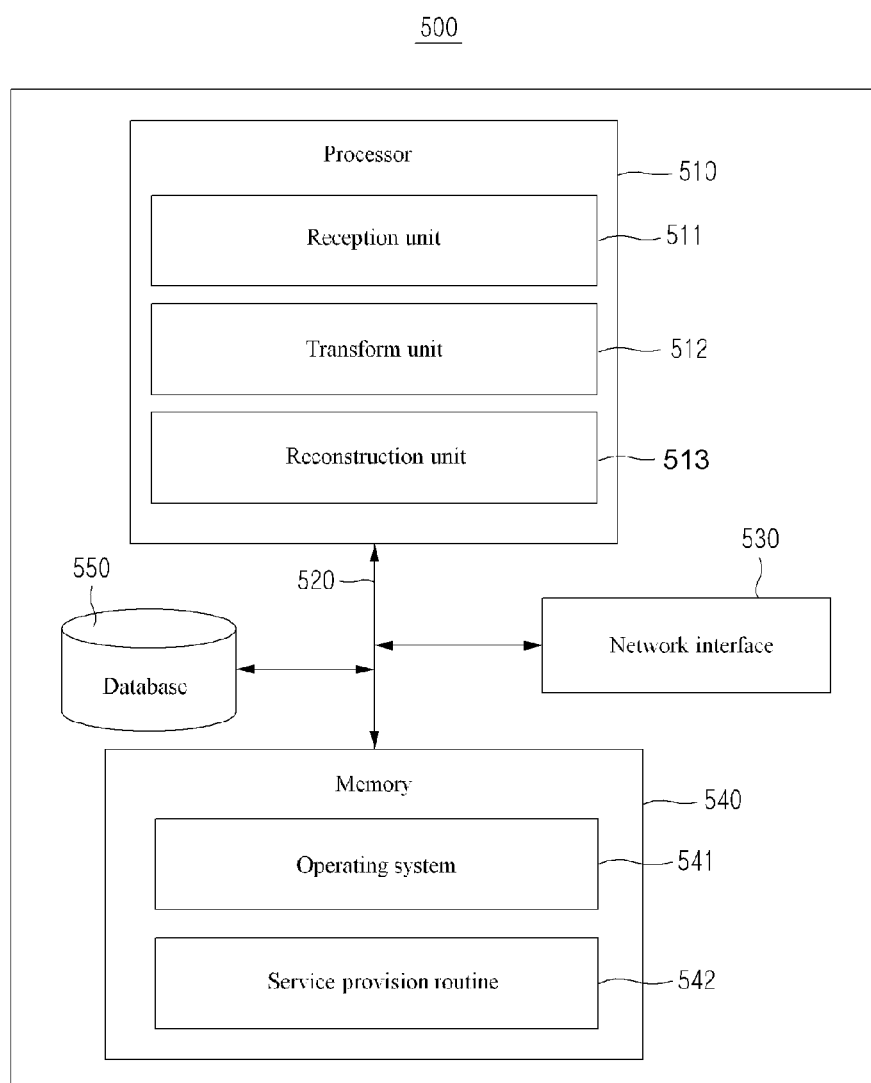
FIG. 5 is a block diagram schematically illustrating a CT system, according to an exemplary embodiment of the inventive concept.

FIG. 5 is a block diagram illustrating a CT system according to an exemplary embodiment of the inventive concept.

A CT system 500 according to an exemplary embodiment of the inventive concept may include a processor 510, a bus 520, a network interface 530, a memory 540, and database 550. The memory 540 may include an operating system 541 and a service provision routine 542. The processor 510 may include a reception unit 511, a transform unit 512, and a reconstruction unit 513. In other embodiments, the CT system 500 may include components of which the number is more than that of FIG. 5. However, it may not be needed to depict conventional components explicitly.

The memory 540 may be a computer-readable recording medium and may include a random access memory (RAM), a read only memory (ROM), and a permanent mass storage device such as a disk drive. Stored in the memory 540 is a program code for the operating system 541 and the service provision routine 542. Such software components may be loaded from a computer-readable recording medium, which is independent of the memory 540, using drive mechanism (not illustrated). The computer-readable recording medium independent of the memory 540 may include a computer-readable recording medium, such as a floppy drive, a disk, a tape, a DVD/CD-ROM drive, a memory card, or the like. In other embodiments, software components may be loaded on the memory 540 through the network interface 530, not the computer-readable record medium.

The bus 520 may enable communication and data transmission to be performed between components of the CT system 500. The bus 520 may be implemented using a high-speed serial bus, a parallel bus, a storage area network (SAN), and/or any other appropriate communication technology.

The network interface 530 may be a computer hardware component for connecting the CT system 500 to a computer network. The network interface 530 may be a network card such as an Ethernet card, an optical transceiver, a wireless frequency transceiver, or other types of devices for transmitting or receiving information. Other embodiments of such network interfaces may be a wireless communication device including Bluetooth, 3G, and wireless-fidelity (Wi-Fi), or the like in mobile computing devices. In other embodiments, a computing device may use the network interface 530 to communicate with an external device such as a server, a mobile phone, or a computing device through wireless connection. The network interface 530 may connect the CT system 500 to a computer network through a wireless or wired connection.

The database 550 may store and retain all necessary information to reconstruct an image. In FIG. 5, an embodiment of the inventive concept is exemplified as the database 550 is implemented in the CT system 500. However, the scope and spirit of the inventive concept may not be limited thereto. For example, the database 550 may be omitted according to a system implementation manner or environment, or the whole or a portion of the database 550 may be implemented with external database constructed on a separate other system.

The processor 510 may process an instruction of a computer program by performing a basic arithmetic operation, a logic operation, and an input/output operation of the CT system 500. The memory 540 or the network interface 530 may provide the instruction to the processor 510 through the bus 520. The processor 510 may be configured to execute program code for the reception unit 511, the transform unit 512, and the reconstruction unit 513. The program code may be stored at a recording device such as the memory 540.

A reception unit 511 may receive low dose X-ray CT data.

A transform unit 512 may transform the low dose X-ray CT data by applying an analytic principle with respect to an optimization approach for low dose imaging in response to receiving the low dose X-ray CT data.

The transform unit 512 may transform the low dose X-ray CT data in the form for iteratively solving an optimization problem included in the optimization approach using a preconditioner. In an image reconstruction method using an analytic principle, the transform unit 512 may apply a differentiated backprojector as the preconditioner, thereby increasing a reconstruction speed. Here, the transform unit 512 may generate DBP data by performing the differentiated backprojector for performing differentiation with respect to projection data and for performing a backprojection process with respect to the differentiated projection data based on a PI-line. The DBP data on the PI-line may have a Hilbert transform relation with the reconstruction image on the PI-line.

In the image reconstruction method using the analytic principle, the transform unit 512 may define operator T as a transform operator for transforming an updated image on Cartesian coordinate into an image on the PI-line. The transform unit 512 may redefine an optimization problem using a projector and a backprojector as an optimization problem using a Hilbert transform operator and a transform operator for transforming an updated image on Cartesian coordinate into an image on the PI-line by applying a differentiated backprojector as a preconditioner to the optimization problem using the projector and the backprojector.

The transform unit 512 may apply a regularization term and may redefine an optimization problem to remove a noise. For a convergence speed that is equal to or greater than a predetermined reference speed, the transform unit 512 may apply an image reconstruction method to the low dose X-ray CT data after applying a Hilbert transform to DBP data to transform the DBP data, to which the Hilbert transform is applied, into a reconstruction image on PI-line or after performing an initial reconstruction using an analytic reconstruction algorithm.

A reconstruction unit 513 may reconstruct a high-quality image by removing a noise included in the low dose X-ray CT data.

According to an embodiment of the inventive concept, operators $\mathcal{H}$ and T may be used instead of using a projector and a backprojector in an iterative reconstruction method using an analytic principle, thereby reducing computational complexities to reduce reconstruction time.

According to an embodiment of the inventive concept, a regularization term may be performed on Cartesian coordinate, thereby applying various kinds of penalty terms in a conventional method to remove a noise.

According to an embodiment of the inventive concept, an optimization problem may be solved through high-speed optimization methods, thereby providing a high-speed new frame in low dose CT image reconstruction fields.

The units (or devices) described herein may be implemented using hardware components, software components, and/or a combination thereof. For example, devices and components described therein may be implemented using one or more general-purpose or special purpose computers, such as, but not limited to, a processor, a controller, an arithmetic logic unit (ALU), a digital signal processor, a microcomputer, a field programmable gate array (FPGA), a programmable logic unit, a microprocessor or any other device capable of responding to and executing instructions in a defined manner. A processing device may run an operating system (OS) and one or more software applications that run on the OS. The processing device also may access, store, manipulate, process, and create data in response to execution of the software. For the sake of easy understanding, an embodiment of the inventive concept is exemplified as one processing device is used; however, one skilled in the art will appreciate that a processing device may include multiple processing elements and multiple types of processing elements. For example, a processing device may include multiple processors or a processor and a controller. In addition, other processing configurations are possible, such as parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums.

The methods according to embodiments may be implemented in the format of program instruction executable through various computing devices and may be recorded in a computer-readable medium. The computer-readable medium may also include program instructions, data files, data structures, and the like independently or in the format of combination. The program instructions recorded in the medium may be those specially designed and constructed for the embodiment or may be well-known and available to those skilled in the computer software arts. Examples of the computer-readable medium may include magnetic media such as hard disks, floppy disks, and magnetic tape; optical media such as CD ROM disks and DVD; magneto-optical media such as floptical disks; and hardware devices that are specialized to store and perform program instructions, such as read-only memory (ROM), random access memory (RAM), flash memory, and the like. Examples of program instructions may include both machine code produced by a compiler and high-level code executed by the computer using an interpreter. The described hardware devices may be configured to operate as one or more software modules to perform the operations of the above-described embodiments, and vice versa Although being described with reference to specific examples and drawings, modifications, additions and substitutions on embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

While the inventive concept has been described with reference to exemplary embodiments, it will be apparent to those skilled in the art that various changes and modifications may be made without departing from the spirit and scope of the present invention. Therefore, it should be understood that the above embodiments are not limiting, but illustrative.

What is claimed is:

1. A method of reconstructing an image, comprising:
receiving low dose X-ray computed tomography (CT) data;
calculating an initial reconstruction image based on the low dose X-ray CT data using a back projection filtration (BPF) algorithm;
calculating differentiated backprojection (DBP) data based on the low dose X-ray CT data using the BPF algorithm;
transforming the initial reconstruction image into a transformed reconstruction image based on a projection on a PI-line that connects two points of a helical trajectory vector in the low dose X-ray CT data;
performing a Hilbert transform on the transformed reconstruction image;
comparing the Hilbert transformed reconstruction image and the DBP data;
determining whether the Hilbert transformed reconstruction image converges with the initial reconstruction image based on the comparison; and
responsive to determining that the Hilbert transformed reconstruction image does not converge with the initial reconstruction image, iteratively updating the Hilbert transformed reconstruction image until the updated Hilbert transformed reconstruction image converges with the initial reconstruction image.

2. The method of claim 1, wherein calculating the initial reconstruction image comprises:
transforming the low dose X-ray CT data in a form for iteratively solving an optimization problem using a preconditioner.

3. The method of claim 1, wherein the DBP data is calculated by performing the differentiated backprojector for performing differentiation with respect to projection data and performing a backprojection process with respect to the differentiated projection data based on the PI-line, and
wherein the DBP data on the PI-line has a Hilbert transform relation with the transformed reconstruction image on the PI-line.

4. The method of claim 1, further comprising:
defining an operator T as a transform operator for transforming an updated image on a Cartesian coordinate into an image on the PI-line.

5. The method of claim 1, wherein iteratively updating the Hilbert transformed reconstruction image comprises:
transforming the Hilbert transformed reconstruction image into a reconstruction image on Cartesian coordinate.

6. The method of claim 5, further comprises:
applying a regularization term and redefining an optimization problem to remove a noise in the reconstruction image on the Cartesian coordinate.

7. A computed tomography (CT) system for reconstructing an image, comprising:
at least one computer processor; and a non-transitory computer readable recording medium storing program instructions, the program instructions when executed by the computer processor cause the computer processor to perform steps comprising:
receive low dose X-ray CT data;
calculate an initial reconstruction image data based on the low dose X-ray CT data using a back projection filtration (BPF) algorithm;
calculate differentiated backprojection (DBP) data based on the low dose X-ray CT data using the BPF algorithm;
transform the initial reconstruction image into a transformed reconstruction image based on a projection on a PI-line that connects two points of a helical trajectory vector in the low dose X-ray CT data;
perform a Hilbert transform on the transformed reconstruction image;
compare the Hilbert transformed reconstruction image and the DBP data;
determine whether the Hilbert transformed reconstruction image converges with the initial reconstruction image based on the comparison; and
responsive to determining that the Hilbert transformed reconstruction image does not converge with the initial reconstruction image, iteratively update the Hilbert transformed reconstruction image until the updated Hilbert transformed reconstruction image converges with the initial reconstruction image.

8. The CT system of claim 7, wherein calculating the initial reconstruction image comprises transforming the low dose X-ray CT data into a form for iteratively solving an optimization problem using a preconditioner.

9. The CT system of claim 7, wherein the DBP data is calculated by performing the differentiated backprojector for performing differentiation with respect to projection data and performing a backprojection process with respect to the differentiated projection data based on the PI-line, and wherein the DBP data on the PI-line has a Hilbert transform relation with the transformed reconstruction image on the PI-line.

10. The CT system of claim 7, wherein the program instructions when executed by the computer processor cause the computer processor to perform further steps comprising defining an operator T as a transform operator for transforming an updated image on Cartesian coordinate into an image on the PI-line.

11. The CT system of claim 7, wherein iteratively updating the Hilbert transformed reconstruction image comprises transforming the Hilbert transformed reconstruction image into a reconstruction image on Cartesian coordinate.

12. The CT system of claim 11, wherein the program instructions when executed by the computer processor cause the computer processor to perform further steps comprising applying a regularization term and redefines an optimization problem to remove a noise in the reconstruction image on the Cartesian coordinate.

13. A non-transitory computer-readable recording medium recorded with an instruction for reconstructing an image by a computer system, the instruction, when executed by the computer system, causing the computer system to perform a method, the method comprising:
receiving low dose X-ray computed tomography (CT) data;
calculating an initial reconstruction image based on the low dose X-ray CT data using a back projection filtration (BPF) algorithm;
calculating differentiated backprojection (DBP) data based on the low dose X-ray CT data using the BPF algorithm;
transforming the initial reconstruction image into a transformed reconstruction image based on a projection on a PI-line that connects two points of a helical trajectory vector in the low dose X-ray CT data;
performing a Hilbert transform on the transformed reconstruction image;
comparing the Hilbert transformed reconstruction image and the DBP data;
determining whether the Hilbert transformed reconstruction image converges with the initial reconstruction image based on the comparison; and
responsive to determining that the Hilbert transformed reconstruction image does not converge with the initial reconstruction image, iteratively updating the Hilbert transformed reconstruction image until the updated Hilbert transformed reconstruction image converges with the initial reconstruction image.

* * * * *

UNITED STATES PATENT AND TRADEMARK OFFICE
CERTIFICATE OF CORRECTION

PATENT NO. : 9,892,527 B2  
APPLICATION NO. : 14/886745  
DATED : February 13, 2018  
INVENTOR(S) : Jong Chul Ye Page 1 of 1

It is certified that error appears in the above-identified patent and that said Letters Patent is hereby corrected as shown below:

In the Claims

Column no: 10, Line(s): 59-60, Claim 5: "on Cartesian coordinate" to read as —on a Cartesian coordinate—

Column no: 12, Line(s): 2, Claim 10: "on Cartesian coordinate" to read as —on a Cartesian coordinate—

Column no: 12, Line(s): 7, Claim 11: "on Cartesian coordinate" to read as —on a Cartesian coordinate—

Signed and Sealed this  
Thirty-first Day of July, 2018

Andrei Iancu  
*Director of the United States Patent and Trademark Office*